United States Patent [19]
Jewett et al.

[11] Patent Number: 5,622,163
[45] Date of Patent: Apr. 22, 1997

[54] COUNTER FOR FLUID DISPENSERS

[75] Inventors: Warren R. Jewett; Frederick A. Ebeling, both of Cary, N.C.

[73] Assignee: IEP Group, Inc., Raleigh, N.C.

[21] Appl. No.: 562,293

[22] Filed: Nov. 22, 1995

Related U.S. Application Data

[63] Continuation-in-part of Ser. No. 346,524, Nov. 29, 1994, Pat. No. 5,544,647.

[51] Int. Cl.$^6$ .............................. A62B 7/00; A61M 11/00
[52] U.S. Cl. .................. 128/200.23; 128/200.14; 128/203.12; 128/203.23
[58] Field of Search ................. 128/200.14, 200.23, 128/202.22, 202.21, 203.12, 203.15, 203.23; 222/30, 36, 37, 38

[56] References Cited

U.S. PATENT DOCUMENTS

| | | | |
|---|---|---|---|
| 3,119,557 | 1/1964 | Chapman | 235/91 R |
| 3,845,883 | 11/1974 | Johnson et al. | 222/30 |
| 4,300,548 | 11/1981 | Jones | 128/204.21 |
| 4,534,345 | 8/1985 | Wetterlin | 128/203.15 |
| 4,677,975 | 7/1987 | Edgar et al. | 128/200.14 |
| 4,817,822 | 4/1989 | Rand et al. | 222/38 |
| 4,947,875 | 8/1990 | Brooks et al. | 131/330 |
| 4,955,371 | 9/1990 | Zamba et al. | 128/200.18 |
| 5,020,527 | 6/1991 | Dessertine | 128/200.23 |
| 5,224,474 | 7/1993 | Bloomfield | 128/201.19 |
| 5,227,764 | 7/1993 | Umemoto | 340/552 |
| 5,228,586 | 7/1993 | Fuchs | 222/38 |
| 5,284,133 | 2/1994 | Burns et al. | 128/200.23 |
| 5,328,597 | 7/1994 | Boldt, Jr. et al. | 210/87 |
| 5,349,945 | 9/1994 | Wass et al. | 128/200.23 |
| 5,363,842 | 11/1994 | Mishelevich et al. | 128/200.14 |
| 5,392,768 | 2/1995 | Johansson et al. | 128/200.14 |
| 5,394,866 | 3/1995 | Ritson et al. | 128/200.14 |
| 5,411,173 | 5/1995 | Weinstein | 222/38 |
| 5,421,482 | 6/1995 | Garby et al. | 222/36 |
| 5,505,192 | 4/1996 | Samiotes et al. | 128/200.14 |
| 5,505,195 | 4/1996 | Wolf et al. | 128/203.15 |
| 5,544,647 | 8/1996 | Jewett et al. | 128/200.23 |

FOREIGN PATENT DOCUMENTS

| | | | |
|---|---|---|---|
| 86/02275 | 4/1986 | WIPO | . |
| 87/04354 | 7/1987 | WIPO | 128/200.23 |
| 90/10470 | 9/1990 | WIPO | 128/203.15 |
| 91/06334 | 5/1991 | WIPO | 128/200.23 |
| 92/17231 | 10/1992 | WIPO | 128/200.23 |

*Primary Examiner*—Vincent Millin
*Assistant Examiner*—Eric P. Raciti
*Attorney, Agent, or Firm*—Kane, Dalsimer, Sullivan, Kurucz, Levy, Eisele and Richard

[57] ABSTRACT

The disclosure is of a device for indicating the number of fluid dispensations remaining in a container for holding and dispensing metered quantities of the fluid. The device is a hermetically-sealed unit which is assembled with the dispenser portion or component of the container and includes microprocessor means for maintaining an inventory of the doses or dispensations remaining of a predetermined number of dispensations. Indicator means signals when the predetermined number of dispensations reaches a level before empty.

11 Claims, 4 Drawing Sheets

COUNTER FOR FLUID DISPENSERS

CROSS-REFERENCE TO RELATED APPLICATION

This application is a continuation-in-part of U.S. patent application Ser. No. 08/346,524 filed Nov. 29, 1994 now U.S. Pat. No. 5,544,647 issued Aug. 13, 1996.

BACKGROUND OF THE INVENTION

1. Field of the Invention

The invention relates to devices for indicating the number of fluid dispensations remaining in a container from which metered dispensations are made.

2. Brief Description of Related Art

A wide variety of fluid dispensers are known and commercially available to dispense metered proportions of a contained fluid from containers. For example, U.S. Pat. No. 3,749,290 describes a trigger actuated dispensing pump assembled with a fluid container. Upon actuation, a measured proportion of the contained fluid is dispensed from the containers.

Of particular importance as fluid dispensers are metered dose inhalers (MDI) employed to administer fluid medications to animals, including humans.

The use of inhalers is well known and the art has developed over the past twenty five years to cover many versions of the basic concept of a "pumping" type medication applicator. The device may be manually pumped (such as described in U.S. Pat. No. 5,284,132) or a pumping like cycle may be utilized. The medication may also be repeatedly released from a pressurized disposable canister to create repeated sprays or inhalations as needed.

Representative of the early inhalers for oral and intranasal administration of medications are those described in, for example, U.S. Pat. Nos. 3,361,306; 3,183,907; 3,565,070; 4,206,758; 4,803,978; 4,934,358; 4,955,371; 5,060,643; and 5,351,683. Representative of nasal-pharyngeal inhalers for large mammals such as a horse is that described in U.S. Pat. No. 5,062,423.

Metered dose inhalers (MDIs) are, at present, the most efficient and best-accepted means for accurately delivering medications in small doses to an animal's respiratory tract. Therapeutic agents commonly delivered by the inhalation route include bronchodilators ($B_2$ agonists and anticholinergics), corticosteroids, and anti-allergics. Inhalation may also be a viable route for anti-infective, vaccinating, systemically acting and diagnostic agents, as well as anti-leukotrienes, anti-proteases and the like.

MDIs are available in several types. Most frequently, MDIs comprise a pressure resistant container (canister) typically filled under super-atmospheric pressures with a product such as a drug dissolved in a liquified propellant, or micronized particles suspended in a liquified propellant. The container is fitted with a metering valve. The valve is movable from an inner (charging) position to an outer (discharging) position. A spring bias holds the valve in the charged position until forced to the discharge position. Actuation of the metering valve allows a metered portion of the canister content to be released, whereby the pressure of the liquified propellant carries the dissolved or micronized drug particles out of the container and to the patient. A valve actuator also functions to direct the aerosol as a spray into the patient's oropharynx. Surfactants are usually dissolved in the aerosol formulation and can serve the dual functions of lubricating the valve and reducing aggregation of micronized particles.

Representative of pharmaceutical formulations for use in metered dose inhalers are those described in U.S. Pat. No. 5,190,029. The MDI devices for administering such pharmaceutical formulations are also well known as seen for example in the descriptions given in U.S. Pat. Nos. 3,361,306; 3,565,070; and 4,955,371 which are incorporated herein by reference thereto.

A disadvantage arising from use of the known devices is that the patient cannot determine the amount of medicament in the aerosol container at any given time. The containers are generally not transparent to view, being light protective of the contents. Shaking them will not always reveal auditory information as to their contents. In an extreme case this could mean that the patient, possibly suffering from severe bronchospasm or like emergency condition and needing a dose of medicament, will find that the aerosol container will not dispense a dose, because its contents have been previously exhausted. The problem has been recognized and consideration given to solutions. For example, U.S. Pat. No. 4,817,822 describes an inhaler device which includes a counting means for indicating the relative emptiness of a container or the number of doses dispensed. However, this inhaler counting mechanism is physically attached to the aerosol container as well as the inhaler, such as by a retaining ring or retaining cap. In one embodiment, the counting means is a separate sleeve fitting on the up-turned bottom of the aerosol container. It is easy to lose, not being integrated with the inhaler, but an ancillary unit slipped over the loose aerosol container. In another embodiment, the counting means requires a secured attachment to the aerosol container neck, which prevents removal of the container from the inhaler, even when empty. The inhaler device is only useful for use with the original aerosol container and can not be used with aerosol refill containers.

The U.S. Pat. No. 5,020,527 presents an improvement over the dose counting means of U.S. Pat. No. 4,817,822 wherein the mechanical counter can be replaced with an electronic counter. The improved inhaler can indicate the number of doses remaining in the aerosol container. However, the device is not fool-proof in operation, which can be a disadvantage in the hands of a severely debilitated, confused or forgetful patient. In households which include small children they have been known to "play" with the MDI's when unsupervised access is possible. Infants can accidentally reset or interfere with established counts in the mechanical devices. For example, the counter can be accidentally reset, obviating its usefulness and, in fact, misleading of the patient as to the true number of doses remaining in the container. Also, the counter can not be automatically reset when a full, new aerosol container (refill) is to be used. This can affect the accuracy of the count carried out.

In addition, the inhaler of the U.S. Pat. No. 5,020,527 still employs a mechanical trigger to actuate the counting means. It is subject to triggering of the counter without actual administration of a dose from the container, for example, when the aerosol container is removed and the inhaler device washed and disinfected, independent of the aerosol container.

These, and other problems associated with the inhalers and other fluid dispensers of the prior art are solved by the present invention, described hereinafter. The device of the invention is economical to manufacture, assemble with fluid containers and disposable when the container is empty, in the same manner currently followed in disposing of the containers.

The device of the invention is intended for use with one fluid container and is disposable with it when the contents are emptied. One need not reset a counter with the errors attendant with such a procedure.

SUMMARY OF THE INVENTION

The invention comprises a device for indicating the number of dispensations remaining in a container for holding and dispensing metered quantities of a fluid, which comprises;

a. a tubular housing, having
 i. a first end;
 ii. a second end;
 iii. a tubular body joining the first and second ends; said tubular body together with the first and second ends defining a hollow chamber;
b. a flexible first closure, closing the first end;
c. a second closure closing the second end;
d. microelectronic means mounted in the chamber, for receiving a signal upon dispensation of a fluid from the container, calculating the number of dispensations remaining in the container and indicating the calculation upon determination of a pre-determined number of remaining dispensations;
e. means for signalling to the microelectronic means upon the occurrence of each dispensation, positioned proximal to the first end of the tubular housing; and
f. means on the second end of the tubular housing for mounting the device on a fluid container assembly in a position where dispensation of a metered dose, simultaneously activates the means for signalling.

The device of the invention is useful to maintain a running inventory of a predetermined quantity of fluid to be dispensed from a container and to signal when a predetermined number of dispensations remains in the container. It is relatively simple to operate, even by young children (6 to 12 years of age). For example, the invention enables one to maintain a count of medication dispensations remaining for use in metered dose inhalers and other fluid dispensers.

BRIEF DESCRIPTION OF THE DRAWINGS

Embodiments of the present invention will be described with reference to the accompanying drawings in which.

DETAILED DESCRIPTION OF THE PREFERRED EMBODIMENTS OF THE INVENTION

Those skilled in the art will gain an understanding of the invention from a reading of the following description of the preferred embodiments when read in conjunction with a viewing of the accompanying drawings of FIGS. 1–5, inclusive.

Figure 1:
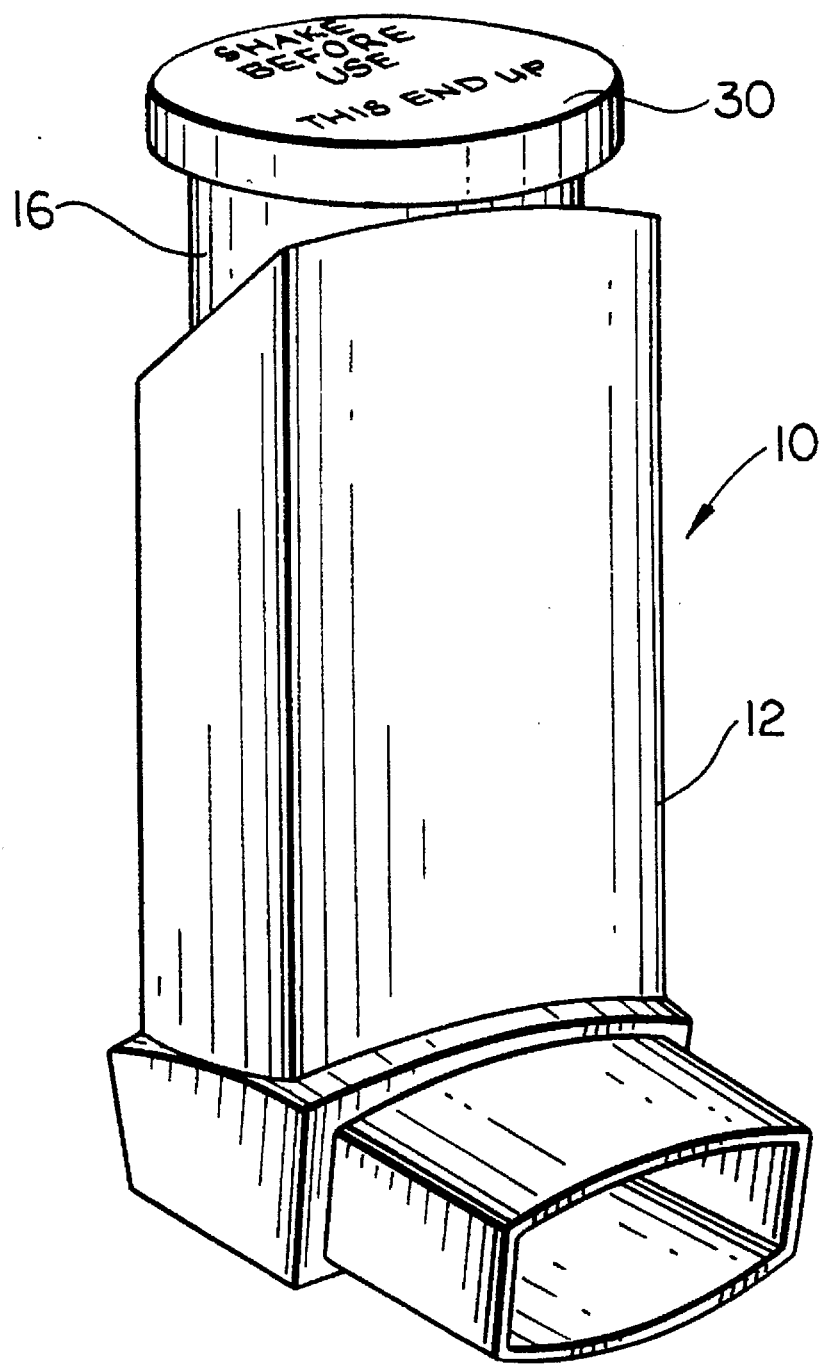
FIG. 1 is a perspective view of an embodiment metered dose inhaler of the invention shown in assembly with a metered dose inhaler aerosol canister.

FIG. 1 is a view-in-perspective of an embodiment assembly 10 of the invention, which comprises an open ended, hollow tube 12 assembled with an aerosol canister 16 upon which there is mounted a device 30 of the invention. The assembly 10 is a metered dose inhaler, as is known and conventional in the prior art, but improved by the inclusion of the device 30, which contains a microelectronic means for dispensations from the canister 16, calculating the number of dispensations remaining in the canister 16 and further, indicating the calculation upon determining that a predetermined number of dispensations remain in the canister 16.

Figure 3:
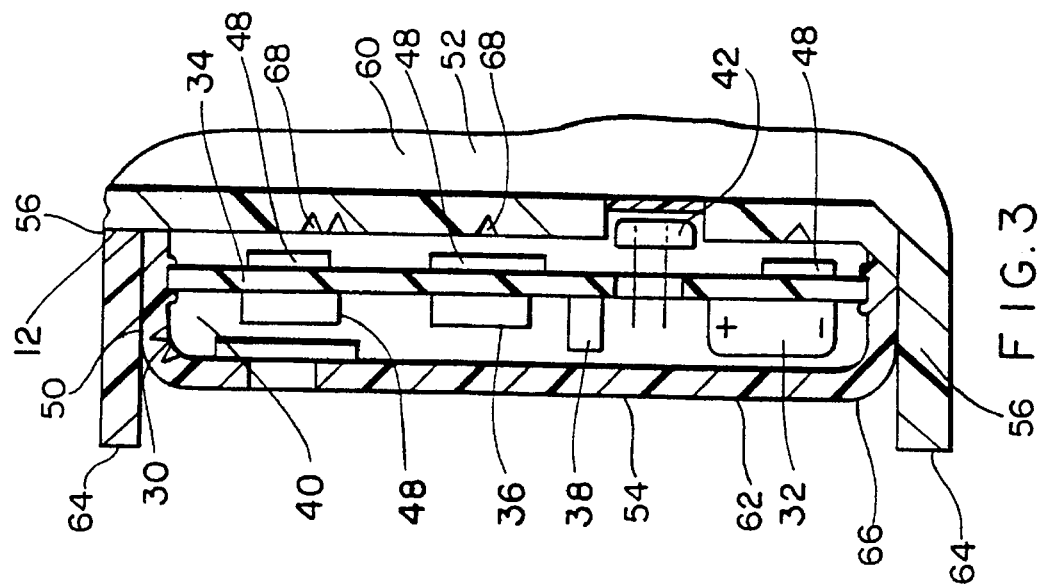
FIG. 3 is an enlarged cross-sectional side view of the count-down component shown in the assembly of FIGS. 1 and 2.
Figure 2:
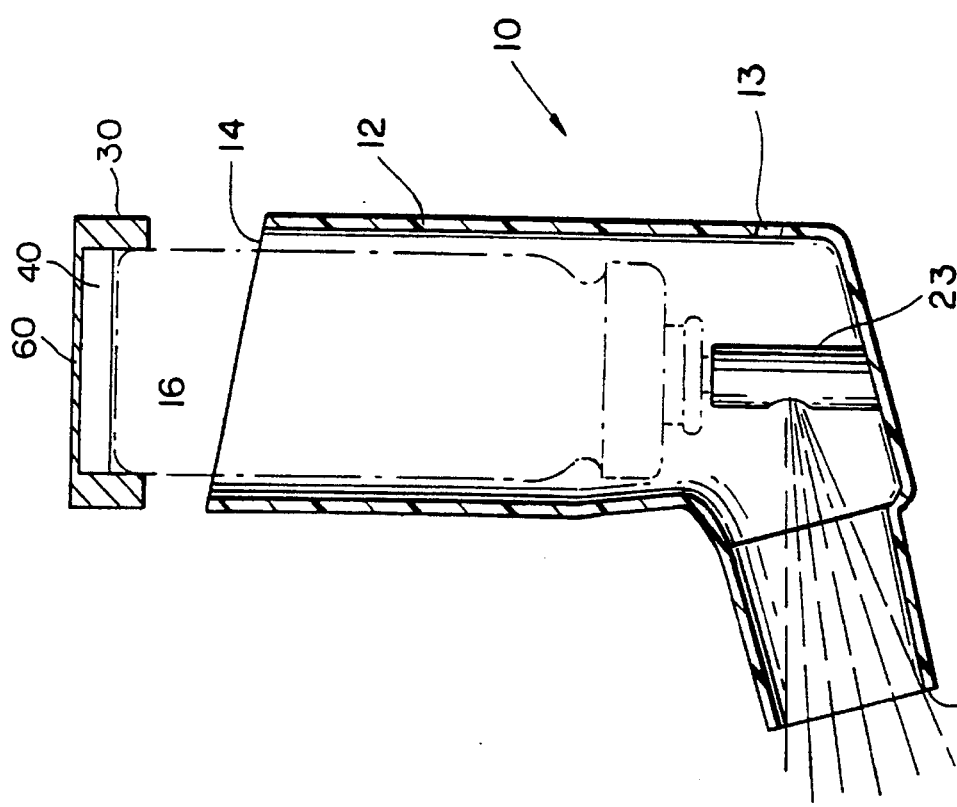
FIG. 2 is a cross-sectional side view of the assembly shown in FIG. 1.

FIG. 2 is a cross-sectional side elevation of the assembly 10 shown in FIG. 1, and depicts further structural details of the embodiment assembly of the invention. As shown in FIG. 2, there is seen a cross-sectional side elevation of an embodiment metered dose inhaler 10 of the invention. The inhaler 10 is essentially a hollow tube 12 having a first open end 14, which by size and configuration is adapted to receive in assembly an aerosol canister 16. A small vent aperture 13 may be advantageous to vent the tube 12 during use, allowing ambient air in. The aerosol canister 16 is fitted with a conventional metering valve (not seen in FIG. 2) and spray stem 18. Such canisters 16 are commercially available from the Bespak Co., North Carolina, U.S.A. They may contain any of the pharmaceutical preparations conventionally used in oral and nasal medicators, such as described for example in the U.S. Pat. No. 5,190,029. The assembled tube 12 and canister 16 locates the canister 16 partially within tube 12 hollow 20. Open end 22 communicates with hollow 20 and is adapted by size and configuration to form a mouthpiece for insertion in the oral cavity of a patient and to couple or sealingly engage with the oral lips for inspiration and expiration of the breath of a mammal. Alternatively, end 22 can be adapted to engage with the patient's nasal passages. Within the hollow 20 is fixedly mounted a spray-directing element 23 which includes a continuous internal conduit 24. The conduit 24 couples with the stem 18 of the aerosol canister 16 and directs a metered dose therefrom out of nozzle 26 as a spray toward the open end 22 of the tube 12 when the canister 16 is pushed downwardly by the user. The valve of canister 16 is activated to release a metered dose. The valve is activated when the patient pushes the canister 16 downward, forcing the stem 18 against the element 23, opening the valve mentioned above. In a preferred embodiment of the invention, the interior walls of tube 12 at end 14 and inward may be closely fitted to the walls of canister 16 (a sliding engagement) so the canister 16 will move freely within hollow 20 until stem 18 is stopped by element 23, but is sufficiently close fitting to avoid escape of aerosol spray through open end 14 during use. As shown in both FIG. 1 and FIG. 2, the up-turned canister 16 slidingly engaged in the hollow 20 through end 14 is accessible to be pushed down on element 23. When depressed upon element 23, the valve on the canister 16 opens to release a metered dose of the aerosol formulation, through stem 18 and conduit 24 to spray from nozzle 26 towards the open end 22 of the tube 12. One dose is released from aerosol canister 16 each time it is fully depressed upon element 23. Release of pressure on canister 16 returns it to the non-depressed position, charging its valve for a further discharge of a dose when the valve is again activated. As shown in FIG. 2 the valve is concealed within the neck of canister 16, and functions when the stem 18 is pushed interiorly of canister 16; the valve itself is not shown in the FIGS. 1–2 being conventional and within the enclosure of the canister 16 itself. As described to this point inhaler assembly 10 is a known device, and can be for example as detailed in the U.S. Pat. No. 3,361,306, incorporated herein by reference thereto. The known inhaler is modified as described hereinafter to manufacture the inhaler assembly 10 of the invention. Integral to canister 16, preferably adhesively attached and non-removable from the exterior of canister 16 in a location on the upturned bottom of canister 16 is a hermetically sealed device 30 for the containment of microelectronic means for determining the number of doses remaining in the canister 16 after each activation and release of a metered dose. The positioning of device 30 on the upturned bottom of canister 16 enables the operator to depress the canister 16 as described above by pressing on the sheet 60 of device 30 with a finger. The containment of the microelectronic counter means within a hermetically sealed device 30 permits the user to remove the canister 16 at any time, with attached device 30 to wash the tube 12 (inside and out) with water, soaps, disinfectants and antiseptic solutions with no damage to or interference with an ongoing count, as will be described more fully hereinafter. This is important, because sprays of many aerosol formulations leave tacky residues which will entrap dust and dirt particles. Some provide a media for the growth of undesired microorganisms. If the growth of these microorganisms is unchecked, they can serve as a source of infection for the patient, and will often introduce pathogens into the patent's respiratory tract. Referring now to FIG. 3, there is seen an enlarged view in cross-section of an embodiment device 30 containing microelectronic means for maintaining an inventory of the doses remaining in canister 16. The FIG. 3 does not show the electrical wiring between component parts, for clarity of the drawing. Hermetically sealed within an interior chamber 40 of the device 30 is a power source 32, for example, a long-life battery such as the conventional and known nickel-cadmium or lithium batteries providing circa 1 to 3.0 volts of electric power. Mounted on a printed circuit board 34 and powered by the power source 32 is an application specific integrated circuit (ASIC) 36 such as a logic array or a microprocessor programmed to process electrical signals from a sensor and trigger a signalling device 38 such as, for example, a tactile alerting device, an audible alarm, a visual indicator, for example, a light emitting diode (LED) or a liquid crystal display (LCD) to give an alphanumeric readout. LCD devices controlled by electronic signals from ASIC 36 are well known and may be for example the type described in U.S. Pat. Nos. 4,804,953; 5,227,899; and 5,227,901. The ASIC 36 is a control means. The ASIC 36 can be a digital integrated circuit serving at least some of the control functions hereinafter enumerated, including timing functions, calculations of the number of dose actuations, memory recordings, visual and auditory indicators. Actuating the ASIC 36 is a switch 42, within chamber 40 of device 30, adjacent to the flexible sheet 60.

Device 30 is a tubular housing 50 having a first end 52, a second end 54 and a tubular body 56 joining the first and second ends 52, 54. The ends 52, 54 together with body 56 defines an interior, hollow chamber 40. The end 52 of the tubular housing 50 is closed with a flexible sheet 60. The end 54 is closed with a sheet or wall 62. A flange 64 circumscribes the periphery 66 of the second end and serves as a means for frictional engagement with canister 16 bottom to attach the device 30. Advantageously, the device 30 is adhesively secured in place on canister 16.

The device 30 housing 50 is preferably made of a transparent or translucent polymeric resin material, and shaped like an inverted cup. The preferred synthetic polymeric resin material for fabricating the device 30 is light transmitting so that when exposed to an interior relatively low level light sources, it appears luminous and illuminates adjacent areas. The resin body of the device 30 may be coated on interior surfaces thereof to selectively reflect inwardly or diffuse light, as desired.

Representative of the synthetic polymeric resins useful to mold housing 50 of device 30 are thermoplastic polyolefins, polyurethanes, polycarbonates and poly(methlmethacrylate), particularly those which are semi-rigid and having some flexibility to facilitate installations and operation as described hereinafter. The interior walls of housing 50 of device 30, defining the chamber 40 may bear a plurality of grooves 68 cooperating to form a Fresnel lens, for magnification of a light display within chamber 40.

The Fresnel lens functions as a light projection device, to enhance light emanating from sources of low level light having varied colors, affording a polychromatic display of the light through the walls of the housing 50 including end 52 sheet 60.

As shown in FIG. 3, the PC board 34 is used to mount one or more light sources such as for example light emitting diodes (LEDs) 48 red or green in color. Preferably when a plurality of light sources are used, these LEDs 48 are disposed substantially equi-distantly around the perimeter of board 34.

Figure 4:
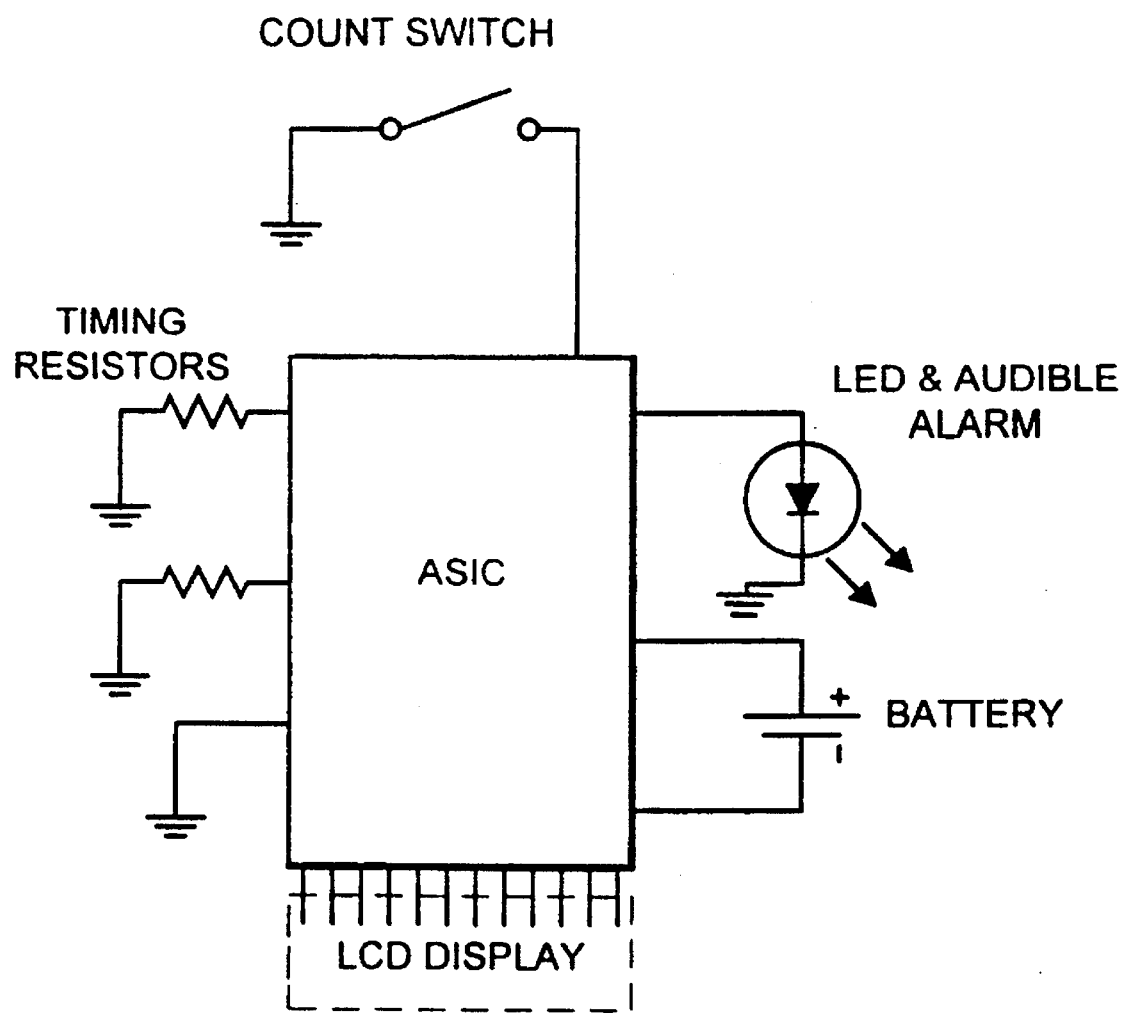
FIG. 4 is an illustration of an embodiment microelectronic circuit component of the microelectronic indicator means shown in FIG. 3.

FIG. 4 is a schematic plan showing embodiment circuitry means for the microprocessor means described above.

The ASIC 36 may be programmed by the manufacturer, to sense and countdown the predetermined number of doses remaining in canister 16 after each use of the assembled apparatus. It can, for example, be programmed to operate as follows:

When a full canister 16 is put into the inhaler assembly 10, with the attached and secured device 30, depressed to cause an initial delivery of a metered dose of medication from the canister 16 as previously described, the ASIC means will start the count process. During normal usage, the canister 16 may be removed at any time for washing the inhaler 10 and then replaced without altering the ongoing count. The dose counter microelectronic means audibly or visually signals after 180 of 200 doses (or any set number) have been dispensed. A red LED 48 may be programmed to flash twice a second for 10 seconds on each use after 180 doses have been administered and this illumination will be seen through the light-transparent sheet 60 or housing 50 of the device 30. After a further 10 doses, for example, are dispensed, for instance at dose 191, an audible tone may sound a number of times after each inhaler 10 use indicating the count of remaining doses, upon reaching the final dose, there can be a long sustained audible tone or constant illumination of LED 48 of perhaps 10 seconds duration.

The application Specific Integrated Circuit (ASIC) 36 is set at manufacture for a total count of for example, 200 doses. Each time the patient depresses the medication canister 16 for an inhaled dose of, for example, Albuterol®, switch 42 is closed by downward digit pressure on sheet 60 of device 30, simultaneously with the downward motion of the canister 16. The switch 42 closure triggers the microelectronic means to subtract "one" from any count. Successive uses to the, for example, 180th dose are carried out in the same way. Starting with the 181st dose delivery, the LED 48 may flash several times after depressing the canister (perhaps 20 flashes in 10 seconds). This visual signal indicates it is time to seek a refill of the prescribed medication. The signal with each successive dose repeats to the final dose remaining, (200th), at which time the LED 48 may be programmed to stay on until the battery exhausts or the canister 16 with attached device 30 is replaced. The device 30 is disposable and can be disposed of with the empty canister 16.

By construction of the device 30, and flexibility of sheet 60 to activate switch 42, thereby triggering a countdown, one can ensure that false counts will not occur while carrying the assembly 10. The micro-switch 42 can be selected to operate, for example, at 3 to 7 lbs. of pressure. The typical pressure required to press canister 16 downward in the prior art assembly of an MDI is about 3 lbs.

As a further alternative, in conjunction with a liquid crystal display (LCD), the ASIC 36 can be programmed to provide a (LCD) giving total number of doses remaining.

Figure 5:
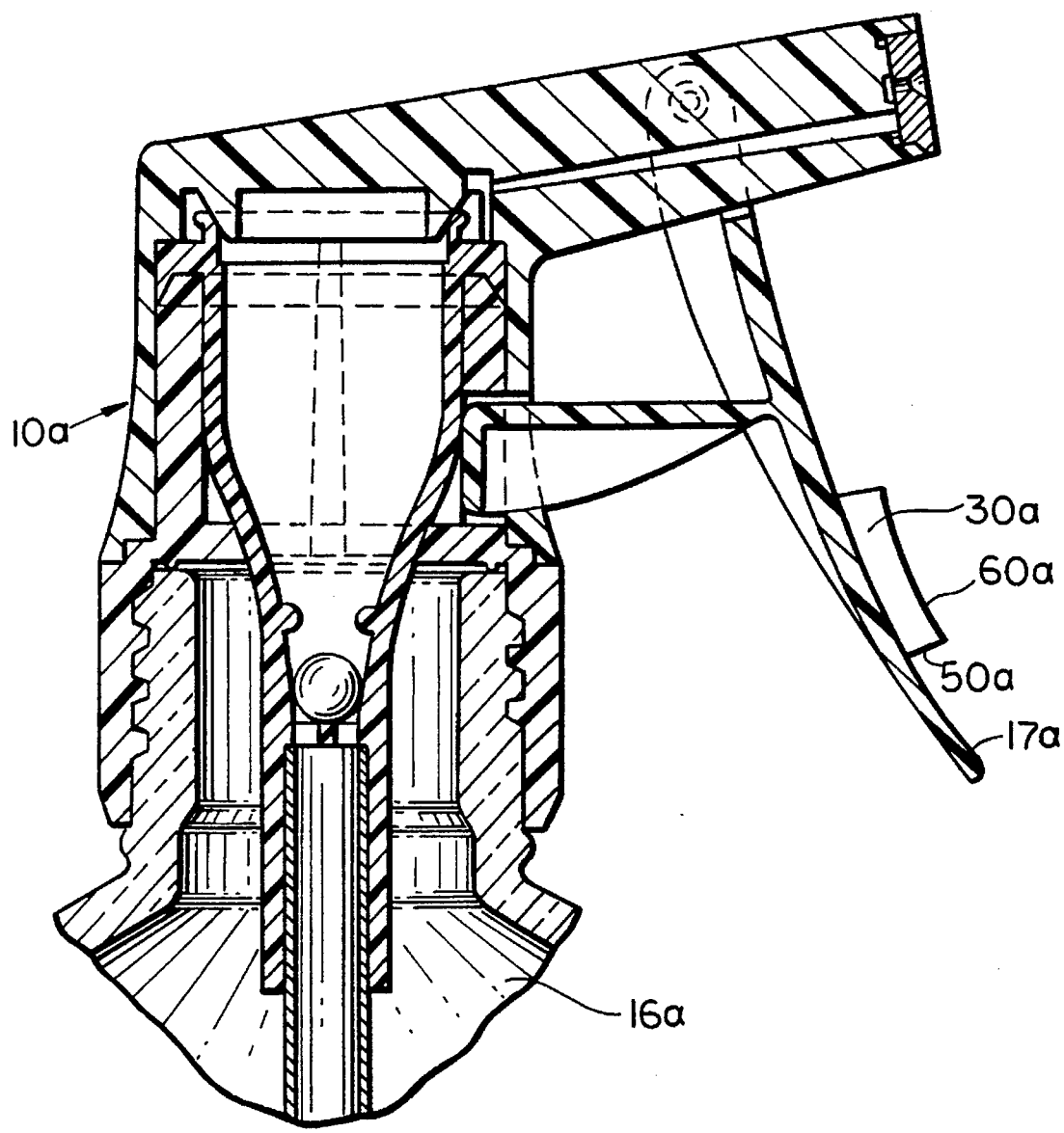
FIG. 5 is a longitudinal sectional view of a pump associated with the neck of a fluid container, as taken from FIG. 9 of U.S. Pat. No. 3,749,290, incorporated herein by reference thereto, and modified to include assembly with the device of the invention shown in FIGS. 1–4.

FIG. 5 is a cross-sectional side elevation of a trigger actuated dispensing pump 10a mounted on a container 16a (shown fragmented). The container 16a may be non-transparent so that one can not visually determine the contents thereof. Adhesively secured to the trigger 17a for actuating the pump 10a is a device 30a, identical in all respects to the device 30 described above. When the trigger 17a is pulled by the operator's finger, a digit placed on sheet 60a of the housing 50a as described above actuates through the switch 42 the ASIC 36 means previously described. As mentioned above, the device 30a can be constructed with a microswitch 42a which will function at any selected pressure, generally within the range of about 3 to 10 lbs., to avoid false counts during operation of the trigger 17a.

What is claimed is:

1. A device for indicating the number of dispensations remaining in a container for holding and dispensing metered quantities of a fluid, which comprises;
    a. a tubular housing, having
        i. a first end;
        ii. a second end;
        iii. a tubular body joining the first and second ends; said tubular body together with the first and second ends defining a hollow chamber;
    b. a flexible first closure, closing the first end;
    c. a second closure closing the second end;
    d. microelectronic means mounted in the chamber, for receiving a signal upon dispensations of a fluid from the container, calculating the number of dispensations remaining in the container and indicating the calculation upon determination of a pre-determined number of remaining dispensations;
    e. means for signalling to the microelectronic means upon the occurrence of each dispensation, positioned proximal to the first end of the tubular housing; and
    f. means on the tubular housing for mounting the device on a fluid container in a position where dispensation of a metered dose simultaneously activates the means for signalling.

2. Device of claim 1 wherein the tubular housing is fabricated from a synthetic polymeric housing, which is at least in part light transmitting therethrough.

3. Device of claim 1 wherein the housing is hermetically sealed.

4. Device of claim 1 which further comprises a switch for sending the signal to the microelectronic means, positioned in the hollow chamber.

5. Device of claim 1 wherein the means for signalling comprises a light-emitting diode, positioned in the hollow chamber.

6. Device of claim 1 wherein the microelectronic means comprises an application Specific Integrated Circuit programmed to indicate the number of fluid doses remaining the container after each dispensation.

7. Apparatus of claim 1 wherein the means of signalling the calculation comprises a liquid crystal display.

8. In an assembly for administration to the respiratory tract of a mammal orally or intranasally, a pharmaceutically active medication, which comprises;
    (a) a hollow closed tube having
        (i) a first open end adapted by size and configuration to receive an aerosol canister containing a predetermined number of unit doses of the medication, in the tube hollow;
        (ii) a second open end adapted by size and configuration to couple with the oral or nasal cavities of a mammal;
    (b) an aerosol canister having a top and a bottom and a metering valve on the canister top for the release of a predetermined number of unit doses of a contained medication for administration to a mammal, positioned in the first open end of the tube; and
    (c) means for the valved release of the predetermined number of unit doses of medication from the aerosol canister; the improvement, which comprises;
    (d) microelectronic means, mounted on the canister bottom and having
        (i) an application Specific Integrated Circuit programmed to receive a signal generated by the valved release of a single unit dose from the aerosol canister and to calculate, upon receiving the signal the number of predetermined unit doses minus the number of doses released; and
        (ii) means to signal the calculation.

9. The assembly of claim 8 wherein the hollow tube is fabricated from a synthetic polymeric resin.

10. The assembly of claim 8 wherein the means for signalling comprises a light-emitting diode.

11. Apparatus of claim 8 wherein the means of signalling the calculation comprises a liquid crystal display.

* * * * *

UNITED STATES PATENT AND TRADEMARK OFFICE
CERTIFICATE OF CORRECTION

PATENT NO. : 5,622,163
DATED : April 22, 1997
INVENTOR(S) : Jewett et al.

It is certified that error appears in the above-identified patent and that said Letters Patent is hereby corrected as shown below:

Column 8,
Line 15, that portion of the text reading "remaining the" should read -- remaining in the --.
Line 22, remove the word "closed".

Signed and Sealed this

Twenty-first Day of June, 2005

JON W. DUDAS
*Director of the United States Patent and Trademark Office*